(12) United States Patent
Dorsch et al.

(10) Patent No.: US 6,197,800 B1
(45) Date of Patent: Mar. 6, 2001

(54) BENZOTHIA(OXA)DIAZOL DERIVATIVES AND THEIR USE AS ENDOTHELIN-RECEPTOR ANTAGONISTS

(75) Inventors: Dieter Dorsch, Ober-Ramstadt; Mathias Osswald, Zwingenberg; Werner Mederski, Erzhausen; Claudia Wilm, Mühltal; Maria Christadler, Rödermark; Claus Jochen Schmitges, Gross-Umstadt, all of (DE)

(73) Assignee: Merck Patent Gesellschaft mi beschraenkter Haftung, Darmstadt (DE)

( * ) Notice: Subject to any disclaimer, the term of this patent is extended or adjusted under 35 U.S.C. 154(b) by 0 days.

(21) Appl. No.: 09/463,311
(22) PCT Filed: Jun. 29, 1998
(86) PCT No.: PCT/EP98/03957
 § 371 Date: Mar. 27, 2000
 § 102(e) Date: Mar. 27, 2000
(87) PCT Pub. No.: WO99/05132
 PCT Pub. Date: Feb. 4, 1999

(30) Foreign Application Priority Data
Jul. 23, 1997 (DE) ................................................ 197 31 571

(51) Int. Cl.$^7$ ..................... C07D 285/14; A61K 31/4245
(52) U.S. Cl. .......................... 514/362; 514/364; 548/126
(58) Field of Search ............................ 548/126; 514/362, 514/364

(56) References Cited
U.S. PATENT DOCUMENTS
6,017,939 * 1/2000 Dorsch .................................. 514/362

* cited by examiner

Primary Examiner—Robert Gerstl
(74) Attorney, Agent, or Firm—Millen, White, Zelano & Branigan, P.C.

(57) ABSTRACT

Novel compounds of the formula I

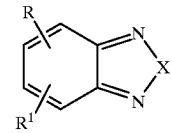

in which

R is

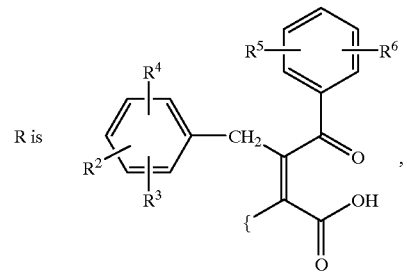

X is O or S, and $R^1$, $R^2$, $R^3$, $R^4$, $R^5$ and $R^6$ have the meaning indicated in patent claim 1, or a tautomeric ring-closed form, and the (E) isomers and their salts exhibit endothelin receptor-antagonistic properties.

21 Claims, No Drawings

BENZOTHIA(OXA)DIAZOL DERIVATIVES AND THEIR USE AS ENDOTHELIN-RECEPTOR ANTAGONISTS

The invention relates to compounds of the formula I

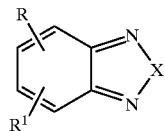

in which
R is

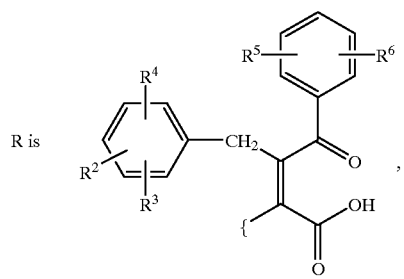

X is O or S,
$R^1$ is H, Hal, OA or A,
$R^2, R^3, R^5, R^6$ independently of one another are H, Hal, A, OA or $R^4$,
$R^4$ is $-O-(CH_2)_n-Cy$,
Cy is cycloalkyl having 3–8 C atoms,
A is alkyl having 1–6 C atoms, in which one or two $CH_2$ groups can be replaced by O or S atoms or by $-CR^5=CR^{5'}$ groups and/or 1–7 H atoms can be replaced by F,
$R^5$ and $R^{5'}$ in each case independently of one another are H, F or A,
Hal is fluorine, chlorine, bromine or iodine,
n is 0, 1 or 2,
or a tautomeric ring-closed form, and the (E) isomers and the salts of all isomers.
The tautomeric ring-closed hydroxylactone form

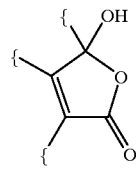

is present if the compounds of the formula I are isolated as carboxylic acids. If the compounds of the formula I are obtained as salts (carboxylates), the open-chain tautomer is obtained.
Similar compounds are disclosed in WO 95/05376.
The invention is based on the object of finding novel compounds having valuable properties, in particular those which can be used for the production of medicaments.
It has been found that the compounds of the formula I and their salts have very valuable pharmacological properties together with good tolerability. In particular, they exhibit endothelin receptor-antagonistic properties and can therefore be employed for the treatment of illnesses such as hypertension, cardiac insufficiency, coronary heart disease, renal, cerebral and myocardial ischaemia, renal insufficiency, cerebral infarct, subarachnoid haemorrhage, arteriosclerosis, pulmonary high blood pressure, inflammations, asthma, prostate hyperplasia, endotoxic shock and in complications after the administration of substances such as, for example, cyclosporin, and also other illnesses associated with endothelin activities.

The compounds exhibit, inter alia, a high affinity for the endothelin subreceptors $ET_A$ and $ET_B$. These actions can be determined by customary in vitro or in vivo methods, such as, for example, described by P. D. Stein et al., J. Med. Chem. 37, 1994, 329–331 and E. Ohlstein et al., Proc. Natl. Acad. Sci. USA 91, 1994, 8052–8056.

A suitable method for the determination of the hypotensive action is described, for example by M. K. Bazil et al., J. Cardiovasc. Pharmacol. 22, 1993, 897–905 and J. Lange et al., Lab Animal 20, 1991, Appl. Note 1016.

The compounds of the formula I can be employed as pharmaceutical active compounds in human and veterinary medicine, in particular for the prophylaxis and/or therapy of cardiac, circulatory and vascular illnesses, especially of hypertension and cardiac insufficiency.

The invention relates to the compounds of the formula I and their salts, and to a process for the preparation of compounds of the formula I according to claim 1 and their salts, characterized in that
a compound of the formula II

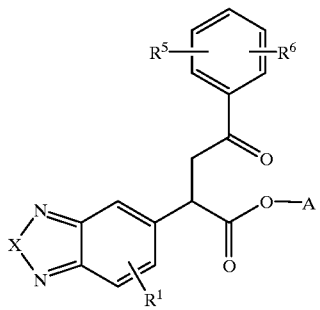

in which
$R^1, R^5, R^6$ and X have the meaning indicated in claim 1, and A is alkyl having 1–4 C atoms or benzyl,
is reacted with a compound of the formula III

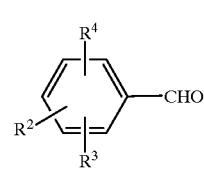

in which
$R^2, R^3, R^4$ have the meaning indicated in claim 1,
and then the ester is cleaved,
and/or a base or acid of the formula I is converted into one of its salts.

For all radicals which occur two or more times, such as, for example, $R^3, R^4$ or $R^5$, it is a condition that their meanings are independent of one another.

Above and below, the radicals or parameters R, X, $R^1, R^2, R^3, R^4, R^5, R^6$, A and n have the meanings indicated under the formulae I to III, if not expressly stated otherwise.

In the above formulae, A is alkyl and has 1 to 6, preferably 1, 2, 3 or 4, C atoms. A is preferably methyl, furthermore ethyl, propyl, isopropyl, butyl, isobutyl, sec-butyl or tert-butyl, and further also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore trifluoromethyl, pentafluoroethyl, allyl or crotyl.

Cycloalkyl is preferably cyclopropyl, cyclobutyl, cyclopentyl, cyclohexyl, cycloheptyl or cyclooctyl.

Hal is preferably F, Cl or Br, but also I.

$R^1$ is preferably H, fluorine, chlorine, bromine, iodine, methoxy, ethoxy, propoxy, methoxymethyl, nitro, amino, formamido, acetamido, sulfonamido, methylsulfonamido, N-methylsulfonamido, cyano and further also formyl.

$R^2$, $R^3$, $R^5$, $R^6$ in each case independently of one another are H, fluorine, chlorine, bromine, iodine, hydroxyl, methoxy, ethoxy, propoxy, butoxy, pentyloxy, hexyloxy, alkyl such as, for example, methyl, ethyl, propyl or isopropyl, furthermore hydroxyl, nitro, amino, N-methylamino, dimethylamino, benzyloxy, phenethyloxy, methylthio, ethylthio, methylsulfinyl, ethylsulfinyl, methylsulfonyl, ethylsulfonyl, phenylsulfinyl, phenylsulfonyl, nitro, amino, methylamino, ethylamino, dimethylamino, diethylamino, formamido, acetamido, N-methylacetamido, N-ethylacetamido, N-propylacetamido, N-butylacetamido, propionylamino, butyrylamino, methylsulfonamido, ethylsulfonamido, propylsulfonamido, butylsulfonamido, N-methylmethylsulfonamido, N-methylethylsulfonamido, N-ethylmethylsulfonamido, N-ethylethylsulfonamido, N-propylmethylsulfonamido, N-propylethylsulfonamido, N-butylmethylsulfonamido, N-butylethylsulfonamido, phenylsulfonamido, (4-methylphenyl)sulfonamido, ureido, methylureido, phenylureido, methoxycarbonylamino, ethoxycarbonylamino, formyl, hydroxymethyl, methoxymethyl, ethoxymethyl, anilino, phenoxycarbonylamino, benzyloxycarbonylamino, benzylsulfonamido, N,N-dimethylureido, 1-piperidinyl-CONH-, 1-pyrrolidinyl-CONH, hydroxyethoxycarbonylamino, methoxyethoxycarbonylamino, carboxymethoxy, carboxyethoxy, methoxycarbonylmethoxy, methoxycarbonylethoxy, hydroxyethoxy, methoxyethoxy, carboxyl, methoxycarbonyl, ethoxycarbonyl, carboxymethyl, methoxycarbonylmethyl or ethoxycarbonylmethyl.

The compounds of the formula I can have one or more chiral centres and therefore occur in various stereoisomeric forms. The formula I includes all these forms.

The Z isomers of the formula I are particularly preferred, i.e. the compounds in which the C=C double bond in the radical R is present in the Z configuration.

Accordingly, the invention relates in particular to those compounds of the formula I in which at least one of the radicals mentioned has one of the preferred meanings indicated above. Some preferred groups of compounds can be expressed by the following subformulae Ia to Ie, which correspond to the formula I and in which the radicals not designated in greater detail have the meaning indicated under the formula I, but in which in Ia $R^1$ is H, X is S, $R^2$, $R^3$, $R^4$, $R^5$ in each case independently of one another are H, Hal, A or OA, A is alkyl having 1–6 C atoms and $R^4$ is cycloalkyl having 3–6 C atoms, in Ib $R^1$ is H.

X is O, $R^2$, $R^3$, $R^4$, $R^5$ in each case independently of one another are H, Hal, A or OA, A is alkyl having 1–6 C atoms and $R^4$ is cycloalkyl having 3–6 C atoms.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and are suitable for the reactions mentioned. In this case, use can also be made of variants which are known per se, but not mentioned here in greater detail.

If desired, the starting substances can also be formed in situ such that they are not isolated from the reaction mixture, but immediately reacted further to give the compounds of the formula I. Compounds of the formula I can preferably be obtained by reacting compounds of the formula II with compounds of the formula III, and then cleaving the ester.

As a rule, the reaction is carried out in an inert solvent, preferably in the presence of a base. A suitable base is, for example, a potassium or sodium alkoxide such as potassium or sodium methoxide, ethoxide or tert-butoxide. Preferred solvents are particularly the underlying alcohols. Depending on the conditions used, the reaction time is between a few minutes and 14 days; the reaction temperature is between approximately 0° and 150°, normally between 20° and 130°.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the solvents mentioned.

As a rule, the starting compounds of the formula II are novel, while as a rule those of the formula III are known.

The compounds of the formula II can be prepared, however, by methods known per se. Thus, for example, ethyl 2-(2,1,3-benzothiadiazol-5-yl)-4-(4-methoxyphenyl)-4-oxobutanoate can be obtained by reaction of ethyl 2-(2,1,3-benzothiadiazol-5-yl)acetate with 2'-bromo-4-methoxyacetophenone in an inert solvent with addition of an acid-binding agent, preferably of an alkali metal or alkaline earth metal hydroxide, carbonate or bicarbonate or another salt of a weak acid of the alkali metals or alkaline earth metals, preferably of potassium, sodium, calcium or caesium. The addition of an organic base such as triethylamine, dimethylaniline, pyridine or quinoline may also be favourable. Preferably, the reaction is carried out at temperatures between 0° and 150°. Suitable inert solvents are those already mentioned above.

The compound methyl 2-(7-methyl-2,1,3-benzothiadiazol-5-yl)acetate can be prepared, for example, from 4,6-dimethyl-2,1,3-benzothiadiazole as follows:

1. Regioselective deprotonation with lithium diisopropylamide and 1,3-dimethyltetrahydropyrimidin-2-one if in THF.
2. Reaction with $CO_2$.
3. Esterification with methyl iodide and potassium carbonate in DMF.

Esters can be hydrolysed, for example, using acetic acid or using NaOH or KOH in water, water-THF or water-dioxane at temperatures between 0 and 100°.

A base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, and further organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, napthalenemono- and disulfonic acids, laurylsulfuric acid. Salts with physiologically unacceptable acids, e.g. picrates, can be used for the isolation and/or purification of the compounds of the formula I.

On the other hand, compounds of the formula I can be converted using bases (e.g. sodium or potassium hydroxide or carbonate) into the corresponding metal salts, in particular alkali metal salts or alkaline earth metal salts, or into the corresponding ammonium salts.

The invention further relates to the use of the compounds of the formula I and/or their physiologically acceptable salts for the production of pharmaceutical preparations, in particular in a non-chemical way. In this case, they can be brought into a suitable dose form together with at least one solid, liquid and/or semi-liquid excipient or auxiliary and, if appropriate, in combination with one or more other active compounds.

The invention further relates to pharmaceutical preparations comprising at least one compound of the formula I and/or one of its physiologically acceptable salts.

These preparations can be used as medicaments in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetate, gelatine, carbohydrates such as lactose or starch, magnesium stearate, talc, petroleum jelly. In particular, tablets, pills, coated tablets, capsules, powders, granules, syrups, juices or drops are used for oral administration, suppositories are used for rectal administration, solutions, preferably oily or aqueous solutions, and furthermore suspensions, emulsions or implants are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more other active compounds, e.g. one or more vitamins.

The compounds of the formula I and their physiologically acceptable salts can be used in the control of illnesses, in particular of hypertension and cardiac insufficiency.

In this case, the substances according to the invention are as a rule preferably administered in doses of between approximately 1 and 500 mg, in particular between 5 and 100 mg per dose unit. The daily dose is preferably between approximately 0.02 and 10 mg/kg of body weight. The specific dose for each patient, however, depends on all sorts of factors, for example on the activity of the specific compound employed, on the age, body weight, general state of health and sex, on the diet, on the time and route of administration, and on the excretion rate, pharmaceutical combination and severity of the particular disease to which the therapy applies. Oral administration is preferred.

Above and below, all temperatures are indicated in ° C. In the following examples, "customary working up" means: if necessary, water is added, the mixture is adjusted, if necessary, to a pH of between 2 and 10 according to the constitution of the final product, and extracted with ethyl acetate or dichloromethane, the organic phase is separated off, dried over sodium sulfate and evaporated, and the residue is purified by chromatography on silica gel and/or by crystallization. $R_f$ values on silica gel; eluent: ethyl acetate/methanol/9:1.

Mass spectrometry (MS):EI (electron impact ionization); $M^+$; FAB (fast atom bombardment) $(M+H)^+$.

EXAMPLE 1

0.368 g of 4-cyclopentyloxy-3,5-dimethoxybenzaldehyde ("A") and 0.52 g of ethyl 2-(2,1,3-benzothiadiazol-5-yl)-4-(4-methoxyphenyl)-4-oxobutanoate, m.p. 89° (obtainable by reaction of 5.5 g of ethyl 2-(2,1,3-benzothiadiazol-5-yl) acetate with 5.5 g of 2'-bromo-4-methoxyacetophenone and 4 g of potassium carbonate in 200 ml of acetone, 18 hours under reflux; ethyl 2-(2,1,3-benzothiadiazol-5-yl)acetate, m.p. 40–41° is obtained by reaction of 24.3 g of ethyl 3,4-diaminophenylacetate and 26.9 ml of thionylaniline in 80 ml of toluene, 4 hours under reflux) are added to a solution of 34 mg of sodium in 10 ml of ethanol and the mixture is heated under reflux for one hour. After addition of 1.4 ml of acetic acid, it is heated for a further 16 hours. The solvent is removed and the residue is worked up in the customary manner. 3-(2,1,3-Benzothiadiazol-5-yl)-4-(4-cyclopentyloxy-3,5-dimethoxy-benzyl)-5-hydroxy-5-(4-methoxyphenyl)-5H-furan-2-one is obtained, FAB 575.

The following are obtained analogously by reaction of "A" with ethyl 2-(2,1,3-benzothiadiazol-5-yl)-4-(3-fluoro-4-methoxyphenyl)-4-oxobutanoate
  3-(2,1,3-benzothiadiazol-5-yl)-4-(4-cyclopentyloxy-3,5-dimethoxybenzyl)-5-hydroxy-5-(3-fluoro-4-methoxyphenyl)-5H-furan-2-one;
with ethyl 2-(2,1,3-benzothiadiazol-5-yl)-4-(2,5-dimethoxyphenyl)-4-oxobutanoate
  3-(2,1,3-benzothiadiazol-5-yl)-4-(4-cyclopentyloxy-3,5-dimethoxybenzyl)-5-hydroxy-5-(2,5-methoxyphenyl)-5H-furan-2-one;
with ethyl 2-(7-methyl-2,1,3-benzothiadiazol-5-yl)-4-(3-fluoro-4-methoxyphenyl)-4-oxobutanoate
  3-(7-methyl-2,1,3-benzothiadiazol-5-yl)-4-(4-cyclopentyloxy-3,5-dimethoxybenzyl)-5-hydroxy-5-(3-fluoro-4-methoxyphenyl)-5H-furan-2-one, m.p. 159–160°.

The following is obtained analogously by reaction of 3-cyclopentyloxy-4,5-dimethoxybenzaldehyde with ethyl 2-(2,1,3-benzothiadiazol-5-yl)-4-(4-methoxyphenyl)-4-oxobutanoate 3-(2,1,3-benzothiadiazol-5-yl)-4-(3-cyclopentyloxy-4,5-dimethoxybenzyl)-5-hydroxy-5-(4-methoxyphenyl)-5H-furan-2-one, FAB 575.

The following are obtained analogously by reaction of 4-cyclopropylmethyloxy-4,5-dimethoxybenzaldehyde with ethyl 2-(2,1,3-benzothiadiazol-5-yl)-4-(4-methoxyphenyl)-4-oxobutanoate 3-(2,1,3-benzothiadiazol-5-yl)-4-(3-cyclopropylmethyloxy-4,5-dimethoxybenzyl)-5-hydroxy-5-(4-methoxyphenyl)-5H-furan-2-one;

with ethyl 2-(2,1,3-benzothiadiazol-5-yl)-4-(3-fluoro-4-methoxyphenyl)-4-oxobutanoate 3-(2,1,3-benzothiadiazol-5-yl)-4-(4-cyclopropylmethyloxy-3,5-dimethoxybenzyl)-5-hydroxy-5-(3-fluoro-4-methoxyphenyl)-5H-furan-2-one;

with ethyl 2-(2,1,3-benzothiadiazol-5-yl)-4-(2,5-dimethoxyphenyl)-4-oxobutanoate 3-(2,1,3-benzothiadiazol-5-yl)-4-(4-cyclopropylmethyloxy-3,5-dimethoxybenzyl)-5-hydroxy-5-(2,5-methoxyphenyl)-5H-furan-2-one and with ethyl 2-(7-methyl-2,1,3-benzothiadiazol-5-yl)-4-(3-fluoro-4-methoxyphenyl)-4-oxobutanoate 3-(7-methyl-2,1,3-benzothiadiazol-5-yl)-4-(4-cyclopropylmethyloxy-3,5-dimethoxybenzyl)-5-hydroxy-5-(3-fluoro-4-methoxyphenyl)-5H-furan-2-one, m.p. 156–158°.

Analogously the Compound 3-(7-methyl-2,1,3-benzothiadiazol-5-yl)-4-(4-cyclohexyloxy-3,5-dimethoxybenzyl)-5-hydroxy-5-(3-fluoro-4-methoxyphenyl)-5H-furan-2-one, m.p. 163–164°, is obtained.

EXAMPLE 2

Equimolar amounts of 0.1N NaOH are added to a suspension of 30 mg of 3-(2,1,3-benzothiadiazol-5-yl)-4-(4-cyclopentyloxy-3,5-dimethoxybenzyl)-5-hydroxy-5-(4-methoxyphenyl)-5H-furan-2-one in 1 ml of methanol and the mixture is stirred at room temperature. The solvent is removed, the residue is partitioned between water and diethyl ether, and the aqueous phase is then lyophilized. Sodium 2-(2,1,3-benzothiadiazol-5-yl)-3-(4-cyclopentyloxy-3,5-dimethoxybenzyl)-4-(4-methoxyphenyl)-4-oxo-2-butenoate is obtained.

By treatment of the furan derivatives mentioned in Example 1 with NaOH, the sodium salts of the corresponding open-chain 4-oxo-2-butenoic acid derivatives are obtained:

sodium 2-(2,1,3-benzothiadiazol-5-yl)-3-(4-cyclopentyloxy-3,5-dimethoxybenzyl)-4-(3-fluoro-4-methoxyphenyl)-4-oxo-2-butenoate;

sodium 2-(2,1,3-benzothiadiazol-5-yl)-3-(4-cyclopentyloxy-3,5-dimethoxybenzyl)-4-(2,5-methoxyphenyl)-4-oxo-2-butenoate;

sodium 2-(7-methyl-2,1,3-benzothiadiazol-5-yl)-3-(4-cyclopentyloxy-3,5-dimethoxybenzyl)-4-(3-fluoro-4-methoxyphenyl)-4-oxo-2-butenoate;

sodium 2-(2,1,3-benzothiadiazol-5-yl)-3-(3-cyclopentyloxy-4,5-dimethoxybenzyl)-4-(4-methoxyphenyl)-4-oxo-2-butenoate;

sodium 2-(2,1,3-benzothiadiazol-5-yl)-3-(3-cyclopropylmethyloxy-4,5-dimethoxybenzyl)-4-(4-methoxyphenyl)-4-oxo-2-butenoate;

sodium 2-(2,1,3-benzothiadiazol-5-yl)-3-(4-cyclopropylmethyloxy-3,5-dimethoxybenzyl)-4-(3-fluoro-4-methoxyphenyl)-4-oxo-2-butenoate;

sodium 2-(2,1,3-benzothiadiazol-5-yl)-3-(4-cyclopropylmethyloxy-3,5-dimethoxybenzyl)-4-(2,5-methoxyphenyl)-4-oxo-2-butenoate and sodium 2-(7-methyl-2,1,3-benzothiadiazol-5-yl)-3-(4-cyclopropylmethyloxy-3,5-dimethoxybenzyl)-4-(3-fluoro-4-methoxyphenyl)-4-oxo-2-butenoate.

The following examples relate to pharmaceutical preparations:

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. The mixture is adjusted to pH 6.8, made up to 1 l and sterilized by irradiation. This solution can be used in the form of eye drops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

Example F

Coated Tablets

Analogously to Example E, tablets are pressed which are then coated in a customary manner with a coating of sucrose, potato starch, talc, traganth and colourant.

Example G

Capsules 2 kg of active compound of the formula I are dispensed into hard gelatine capsules in a customary manner such that each capsule contains 20 mg of the active compound.

Example H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

What is claimed is:

1. A compound of formula I

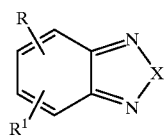

wherein

R is

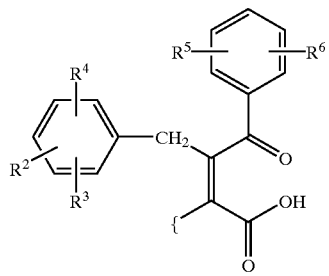

X is O or S,
R¹ is H, Hal, OA or A,
R², R³, R⁵, R⁶ independently of one another are H, Hal, A, OA or R⁴,
R⁴ is —O—(CH₂)$_n$—Cy,
Cy is cycloalkyl having 3–8 C atoms,
A is alkyl having 1–6 C atoms, wherein one or two CH₂ groups can be replaced by O or S atoms or by —CR⁵=CR⁵' groups and/or 1–7 H atoms can be replaced by F,
R⁵ and R⁵' in each case independently of one another are H, F or A,
Hal is fluorine, chlorine, bromine or iodine,
n is 0, 1 or 2, or an (E) or (Z) isomer thereof or a tautomeric ring-closed form, or a salt thereof.

2. A compound of formula I according to claim 1 that is
a) 2-(2,1,3-benzothiadiazol-5-yl)-3-(4-cyclopentyloxy-3,5-dimethoxybenzyl)-4-(4-methoxyphenyl)-4-oxo-2-butenoic acid;
b) 2-(2,1,3-benzothiadiazol-5-yl)-3-(4-cyclopentyloxy-3,5-dimethoxybenzyl)-4-(3-fluoro-4-methoxyphenyl)-4-oxo-2-butenoic acid;
c) 3-(2,1,3-benzothiadiazol-5-yl)-4-(4-cyclopentyloxy-3,5-dimethoxybenzyl)-5-hydroxy-5-(4-methoxyphenyl)-5H-furan-2-one;
d) 3-(2,1,3-benzothiadiazol-5-yl)-4-(4-cyclopentyloxy-3,5-dimethoxybenzyl)-5-hydroxy-5-(3-fluoro-4-methoxyphenyl)-5H-furan-2-one;
e) 3-(2,1,3-benzothiadiazol-5-yl)-4-(3-cyclopentyloxy-4,5-dimethoxybenzyl)-5-hydroxy-5-(3-fluoro-4-methoxyphenyl)-5H-furan-2-one;
f) 3-(7-methyl-2,1,3-benzothiadiazol-5-yl)-4-(4-cyclopentyloxy-3,5-dimethoxybenzyl)-5-hydroxy-5-(3-fluoro-4-methoxyphenyl)-5H-furan-2-one; or a salt thereof.

3. A process for the preparation of a compound of formula I according to claim 1, or a physiologically acceptable salt thereof, comprising reacting a compound of formula II

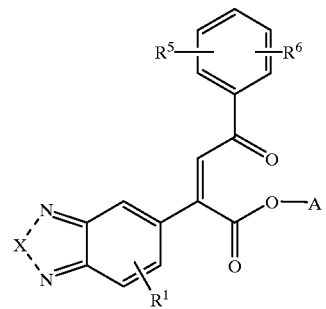

wherein
R¹, R⁵, R⁶ and X have the meaning indicated in claim 1, and
A is alkyl having 1–4 C atoms or benzyl,
with a compound of formula III

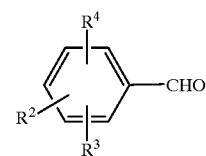

wherein
R², R³, R⁴ have the meaning indicated in claim 1, and then the ester is cleaved,
optionally, a base or acid of formula I is converted into one of its salts.

4. A process for the production of pharmaceutical preparations, comprising bringing a compound of formula I according to claim 1 or a physiologically acceptable salt thereof into a suitable dose form together with at least one solid, liquid or semi-liquid excipient or auxiliary.

5. A composition comprising at least one compound of formula I according to claim 1, or a physiologically acceptable salt thereof, and a pharmaceutically acceptable excipient.

6. A method of treating hypertension, cardiac insufficiency, renal insufficiency, cerebral infarct, coronary heart disease, renal, cerebral and myocardial ischemia, subarachnoid haemorrhage, inflammations, asthma or endotoxic shock comprising administering a therapeutically effective amount of a compound of formula I according to claim 1.

7. A composition comprising at least one compound according to claim 2, or a physiologically acceptable salt thereof, formula I according to claim 1 and a pharmaceutically acceptable excipient.

8. A composition comprising a compound according to claim 2, or a physiologically acceptable salt thereof, and a pharmaceutically acceptable excipient.

9. A method of treating hypertension, cardiac insufficiency, renal insufficiency, cerebral infarct, coronary heart disease, renal, cerebral and myocardial ischaemia, subarachnoid haemorrhage, inflammations, asthma or endotoxic shock comprising administering a therapeutically effective amount of a compound according to claim 2.

10. A compound according to claim 1, wherein R¹ is H; X is S; R², R³, R⁴, and R⁵ are, in each case independently of one another, H, Hal, A or OA; A is alkyl having 1–6 C atoms; and Cy is cycloalkyl having 3–6 C atoms.

11. A compound according to claim 1, wherein $R^1$ is H; X is O; $R^2$, $R^3$, $R^4$, and $R^5$ are, in each case independently of one another, H, Hal, A or OA; A is alkyl having 1–6 C atoms; and Cy is cycloalkyl having 3–6 C atoms.

12. A compound according to formula I of claim 1, wherein the compound is a Z isomer.

13. A compound according to claim 2, wherein the compound is a Z isomer.

14. A compound according to claim 10, wherein the compound is a Z isomer.

15. A compound according to claim 11, wherein the compound is a Z isomer.

16. A composition comprising a compound according to claim 10, or a physiologically acceptable salt thereof, and a pharmaceutically acceptable excipient.

17. A composition comprising a compound according to claim 11, or a physiologically acceptable salt thereof, and a pharmaceutically acceptable excipient.

18. A method of treating hypertension or cardiac insufficiency comprising administering a therapeutically effective amount of a compound according to formula I of claim 1.

19. A method of treating hypertension or cardiac insufficiency comprising administering a therapeutically effective amount of a compound according to claim 2.

20. A method of treating hypertension or cardiac insufficiency comprising administering a therapeutically effective amount of a compound according to claim 10.

21. A method of treating hypertension or cardiac insufficiency comprising administering a therapeutically effective amount of a compound according claim 11.

\* \* \* \* \*

UNITED STATES PATENT AND TRADEMARK OFFICE
CERTIFICATE OF CORRECTION

PATENT NO.     : 6,197,800 B1
DATED          : March 6, 2001
INVENTOR(S)    : Dieter Dorsch et al.

It is certified that error appears in the above-identified patent and that said Letters Patent is hereby corrected as shown below:

<u>Column 10,</u>
Line 53, amend claim 7 as follows:
Delete "formula I according to claim 1".

Signed and Sealed this

Nineteenth Day of November, 2002

Attest:

Attesting Officer

JAMES E. ROGAN
*Director of the United States Patent and Trademark Office*